(12) United States Patent
Heinrichs et al.

(10) Patent No.: US 8,892,203 B2
(45) Date of Patent: Nov. 18, 2014

(54) EMERGENCY RESPONSE BACKBOARD WITH INTEGRATED SCALE

(76) Inventors: John R. Heinrichs, North Pole, AK (US); Daniel Peter Lepley, Fairbanks, AK (US); Donovan Patrick Glade, North Pole, AK (US); Travis Wayne Stewart, North Pole, AK (US); Sheridan Heinrichs, North Pole, AK (US)

(*) Notice: Subject to any disclaimer, the term of this patent is extended or adjusted under 35 U.S.C. 154(b) by 47 days.

(21) Appl. No.: 13/444,387

(22) Filed: Apr. 11, 2012

(65) Prior Publication Data

US 2012/0259378 A1    Oct. 11, 2012

Related U.S. Application Data

(60) Provisional application No. 61/474,072, filed on Apr. 11, 2011.

(51) Int. Cl.
*A61N 1/39* (2006.01)
*G01G 19/52* (2006.01)
*G01G 19/44* (2006.01)

(52) U.S. Cl.
CPC .............. *G01G 19/445* (2013.01); *G01G 19/52* (2013.01); *A61N 1/3925* (2013.01); *A61N 1/3993* (2013.01)
USPC .................................................. 607/6; 607/5

(58) Field of Classification Search
CPC .... A61G 1/04; A61G 1/00; A61G 2007/0527
USPC ....................................................... 607/5–9
See application file for complete search history.

(56) References Cited

U.S. PATENT DOCUMENTS

| | | | | |
|---|---|---|---|---|
| 5,393,938 | A * | 2/1995 | Bumbalough | 177/144 |
| 5,749,374 | A * | 5/1998 | Schneider, Sr. | 128/870 |
| 5,780,781 | A * | 7/1998 | Berger et al. | 177/126 |
| 6,447,465 | B1 | 9/2002 | Sherman et al. | |
| 6,616,620 | B2 | 9/2003 | Sherman et al. | |
| 6,680,442 | B1 * | 1/2004 | Rynd et al. | 177/140 |
| 6,869,408 | B2 | 3/2005 | Sherman et al. | |
| 6,939,315 | B2 | 9/2005 | Sherman et al. | |
| 7,008,388 | B2 | 3/2006 | Sherman et al. | |
| 7,056,296 | B2 | 6/2006 | Sherman et al. | |
| 7,131,953 | B2 | 11/2006 | Sherman et al. | |
| 7,166,082 | B2 | 1/2007 | Sherman et al. | |
| 7,199,311 | B1 * | 4/2007 | Buckner et al. | 177/144 |
| 7,360,264 | B2 | 4/2008 | Tomcany | |
| 7,722,554 | B2 | 5/2010 | Sherman et al. | |
| 2002/0177793 | A1 * | 11/2002 | Sherman et al. | 601/41 |
| 2003/0009115 | A1 | 1/2003 | Sherman et al. | |

(Continued)

OTHER PUBLICATIONS

AEDPRO and AEDPROa-w Operator's Guide, Zoll Advancing Resuscitation, Jun. 2009.

(Continued)

*Primary Examiner* — Joseph Dietrich
(74) *Attorney, Agent, or Firm* — Kunzler Law Group, PC

(57) ABSTRACT

An apparatus, system, and method are disclosed for weighing an individual on a backboard. The backboard is configured to support a supine individual during transportation. An upper surface of the backboard is configured to receive the supine individual. A scale is embedded within the backboard beneath the upper surface. The embedded scale is configured to determine a weight of the supine individual in response to the upper surface receiving the supine individual.

20 Claims, 5 Drawing Sheets

(56) References Cited

U.S. PATENT DOCUMENTS

| | | |
|---|---|---|
| 2004/0002667 A1 | 1/2004 | Sherman et al. |
| 2004/0006290 A1 | 1/2004 | Sherman et al. |
| 2004/0030271 A1 | 2/2004 | Sherman et al. |
| 2004/0225238 A1 | 11/2004 | Sherman et al. |
| 2005/0165335 A1 | 7/2005 | Sherman et al. |
| 2006/0225213 A1 | 10/2006 | Tomcany |
| 2007/0124858 A1 | 6/2007 | Ahlman |
| 2007/0270725 A1 | 11/2007 | Sherman et al. |
| 2008/0163426 A1 | 7/2008 | Tomcany |
| 2009/0069726 A1 | 3/2009 | Sherman et al. |

OTHER PUBLICATIONS

MSeries Bluetooth/RS-232 Enhanced Data Communication, Zoll Advancing Resuscitation, 2007.

MSeries Operator's Guide, Zoll Advancing Resuscitation, Aug. 2007.

AutoPulse Resuscitation System Model 100 User Guide, Zoll Advancing Resuscitation, 2009.

* cited by examiner

EMERGENCY RESPONSE BACKBOARD WITH INTEGRATED SCALE

CROSS-REFERENCES TO RELATED APPLICATIONS

This application claims priority to U.S. Provisional Patent Application No. 61/474,072 entitled "EMERGENCY RESPONSE BACKBOARD WITH INTEGRATED SCALE" and filed on Apr. 11, 2011 for John R. Heinrichs, et al., which is incorporated herein by reference.

FIELD

BACKGROUND

This invention relates to backboards and more particularly relates to medical backboards for spinal immobilization.

1. Description of the Related Art

The dosage for many medical treatments depends on the weight of an individual receiving the treatment. For example, the pediatric dosage of atropine varies by weight of the individual receiving treatment and also varies by the intended use, to treat bradycardia or to treat organophosphate poisonings. Similarly, the dosage of dopamine to treat cardiogenic shock and the dosages of epinephrine to treat allergic reactions, asthma attacks, and cardiac arrest also vary by the weight and age of the individual receiving the treatment.

It can be particularly difficult to ascertain the weight of an individual in an emergency medical situation. Despite this difficulty, dosages for more than half of the medications listed in typical emergency response standing orders are based on an individual's weight. Treatments using defibrillators and certain other medical devices also depend on an individual's weight.

Emergency response technicians typically use a color-coded measuring tape for pediatric patients, such as a Broselow™ tape, to estimate an individual's weight based on the individual's height. This is currently the primary emergency medical device used to estimate the weight of a patient, and it is typically used for pediatric patients. Height is often an inaccurate indicator of weight, and can result in overdosing or underdosing of an individual. More accurate measurements of weight, however, are frequently unavailable in an emergency medical situation. Even if a traditional scale is available, it is often too dangerous and time restrictive to move an individual to the scale, as individuals in emergency medical situations are typically immobilized and are often in need of urgent care.

Without an accurate measurement of weight, emergency response technicians can administer an improper dosage of a medical treatment to an individual. At best, an improper dosage can be ineffective. At worst, an improper dosage can be dangerous or even fatal.

SUMMARY

From the foregoing discussion, it should be apparent that a need exists for an apparatus, system, and method that accurately measure a weight of an individual. Beneficially, such an apparatus, system, and method would accurately measure a weight of a supine individual, even in emergency situations.

The present invention has been developed in response to the present state of the art, and in particular, in response to the problems and needs in the art that have not yet been fully solved by currently available emergency weight measurement systems. Accordingly, the present invention has been developed to provide an apparatus, system, and method for weighing an individual that overcome many or all of the above-discussed shortcomings in the art.

The apparatus to weigh an individual is provided with a backboard, an upper surface of the backboard, and a scale embedded within the backboard. In one embodiment, the backboard is configured to support a supine individual during transportation. The upper surface of the backboard, in certain embodiments, is configured to receive the supine individual. The embedded scale, in one embodiment, is configured to determine a weight of the supine individual in response to the upper surface receiving the supine individual.

In a further embodiment, the apparatus includes an electronic display device disposed on the backboard. The electronic display device, in one embodiment, is configured to display the determined weight of the supine individual. In another embodiment, the apparatus includes a communications module embedded within the backboard. The communications module, in certain embodiments, is configured to communicate the determined weight of the supine individual to an electronic device that is remote from the backboard.

The electronic device, in one embodiment, is configured to determine a dosage for a treatment for the supine individual based on the determined weight of the supine individual. For example, in one embodiment, the electronic device may comprise a defibrillator configured to receive the determined weight of the supine individual and the dosage may comprise a setting for an amount of electrical energy that the defibrillator delivers to the supine individual, or the like. In another embodiment, the treatment may comprise a medication and the electronic device may be configured to display the determined dosage of the medication to a user of the electronic device.

In one embodiment, the apparatus includes one or more user interface devices disposed on the backboard. The one or more user interface devices, in a further embodiment, are configured to receive input from a user of the backboard. In another embodiment, the one or more user interface devices are configured to initiate one or more actions, such as powering the scale on and off, setting measurement units for the determined weight, configuring communications settings for the scale, locking the determined weight on an electronic display device, and/or clearing the determined weight from an electronic display device. In a further embodiment, the apparatus includes one or more input/output ports integrated with the backboard. The one or more input/output ports, in certain embodiments, are configured to receive sensor data for the supine individual from one or more additional diagnostic sensors.

The apparatus, in one embodiment, includes a weight support structure interfacing with the upper surface to distribute the weight of the supine individual onto the embedded scale. The weight support structure, in certain embodiments, comprises a plurality of raised ribs, each raised rib in physical communication with a portion of the scale to support the weight of the supine individual. In another embodiment, the weight support structure comprises a frame that supports at least a portion of the upper surface supporting the weight of the supine individual and distributes the weight of the supine individual onto the embedded scale.

In one embodiment, the upper surface and the scale are removable from the backboard. In a further embodiment, the upper surface and the scale are configured to determine a weight of a supine individual independently from the backboard. In another embodiment, at least a portion of the upper surface and the scale is flexible allowing the upper surface and the scale to be compacted by rolling and/or folding the upper surface and the scale.

The scale, in one embodiment, comprises one or more load cells configured to convert the weight of the supine individual into one or more electrical signals. The one or more load cells, in various embodiments, may be selected from the group consisting of strain gauge load cells, hydraulic load cells, piezoelectric load cells, and/or other load cells that convert weight into one or more electrical signals.

In one embodiment, the backboard comprises a full body backboard sized to support a horizontal length of the supine individual. The backboard, in a further embodiment, includes a plurality of handles disposed along a perimeter of the backboard to facilitate lifting and transporting the supine individual using the backboard. The upper surface, in certain embodiments, is at least partially flexible such that the weight of the supine individual at least partially deforms the upper surface allowing the scale to determine the weight of the supine individual. In another embodiment, the upper surface comprises a waterproof material that protects the scale from liquid. In a further embodiment, the upper surface comprises an electrical insulator that protects the scale from electric current.

A system of the present invention is also presented to weigh an individual. The system, in certain embodiments, includes a backboard, an electronic device, an upper surface of the backboard, a scale embedded within the backboard, and a communications module embedded within the backboard.

The backboard, in one embodiment, is configured to support a supine individual during transportation. In a further embodiment, the electronic device is remote from the backboard. The upper surface of the backboard, in one embodiment, is configured to receive the supine individual. The embedded scale, in certain embodiments, is configured to determine a weight of the supine individual in response to the upper surface receiving the supine individual. The communications module, in one embodiment, is configured to communicate the determined weight of the supine individual to the electronic device.

In a further embodiment, the electronic device is configured to determine a dosage for a treatment for the supine individual based on the determined weight of the supine individual. The electronic device, in certain embodiments, may comprise a defibrillator configured to receive the determined weight of the supine individual and the dosage may comprise a setting for an amount of electrical energy that the defibrillator delivers to the supine individual, or the like. In another embodiment, the treatment may comprise a medication and the electronic device may be configured to display the determined dosage of the medication to a user of the electronic device.

A method of the present invention is also presented for forming a backboard with an integrated scale. In one embodiment, the method includes forming a backboard configured to support a supine individual during transportation. The method, in another embodiment, includes embedding a scale within the backboard, the embedded scale configured to determine a weight of the supine individual in response to the backboard receiving the supine individual. In a further embodiment, the method includes forming an upper surface of the backboard, the upper surface configured to receive the supine individual, the scale embedded beneath the upper surface.

In other embodiments, the method may include forming and/or installing other elements of the described apparatus and system. For example, in certain embodiments, the method may include one or more of disposing one or more electronic display devices on the backboard, disposing one or more user interface devices on the backboard, embedding a communications module within the backboard in communication with the scale, configuring an electronic device remote from the backboard for interfacing with the communications module, embedding a weight support structure within the backboard interfacing with the upper surface and the scale, forming a plurality of handles along a perimeter of the backboard, and/or other steps for forming or manufacturing a backboard as described herein.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1:
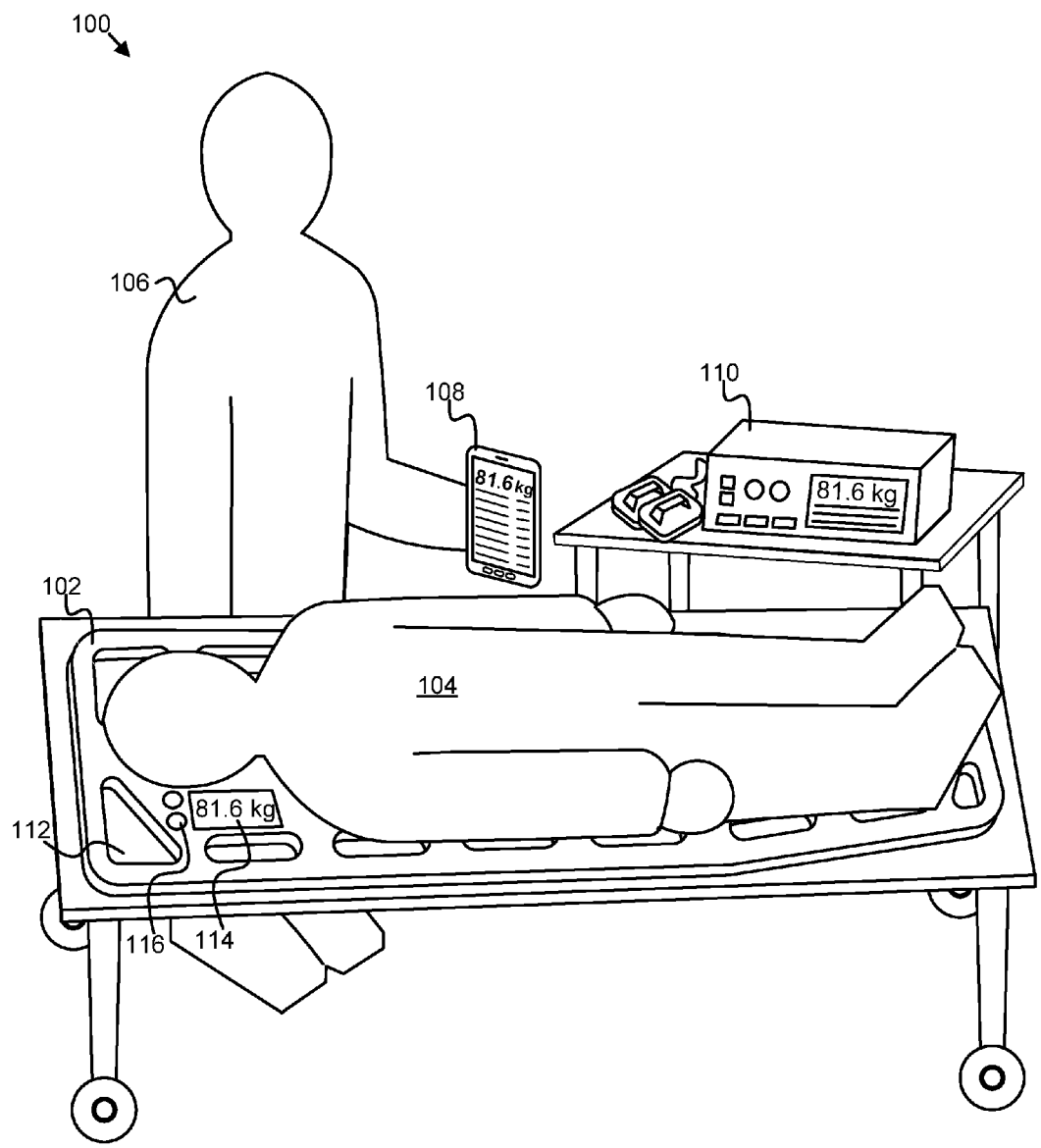
FIG. 1 is a schematic block diagram illustrating one embodiment of a system to weigh an individual on a backboard in accordance with the present invention.

As will be appreciated by one skilled in the art, aspects of the present invention may be embodied as an apparatus, system, method, or computer program product. Accordingly, certain aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the software portions are stored on one or more computer readable mediums.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing.

More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Aspects of the present invention are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and/or computer program products according to various embodiments of the present invention. In this regard, certain blocks in the schematic flowchart diagrams and/or schematic block diagrams may represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that certain blocks of the block diagrams and/or flowchart diagrams, and combinations of blocks in the block diagrams and/or flowchart diagrams, can be implemented by special purpose hardware-based systems that perform the specified functions or acts, or combinations of special purpose hardware and computer instructions.

FIG. 1 depicts one embodiment of a system 100 to weigh an individual 104 on a backboard 102. In the depicted embodiment, the backboard 102 includes an integrated scale, one or more handles 112, an electronic display device 114, and one or more user interface devices 116. In certain embodiments, the backboard 102 and integrated scale communicate a determined weight of the individual 104 to one or more electronic devices 108, 110, such as a mobile device 108, a defibrillator 110, or the like. A medical technician 106, in one embodiment, uses a determined weight of the individual 104 to medically treat the individual 104.

The backboard 102 with an integrated scale, in certain embodiments, allows a medical technician 106 to quickly and accurately determine a weight of an individual 104, even in emergency situations, so that the medical technician 106 can provide treatment to the individual 102 at the correct dosage level. In a further embodiment, integrating a scale with a backboard 102 is also efficient in emergency response situations, as the scale is transported with the backboard 102 to and from the field without the need for additional equipment or storage space. Additionally, once the individual 104 is placed on the backboard 102, the scale is also available for use in the field, in an ambulance, or in a hospital, without the need to remove the individual 104 from the backboard 102.

In one embodiment, the backboard 102 supports the individual 104 during transportation, as the individual 104 lays in a supine position on the backboard 102. The backboard 102, in certain embodiments, immobilizes the spine of the individual 104 to secure an injured individual 104, an ill individual 104, an infirm individual 104, or another individual 104 in need of transportation and/or immobilization, and to help prevent additional injury to the individual 104 during transportation. For example, the backboard 102 may include straps, clips, buckles, a head immobilizer, and/or other securing mechanisms to secure the individual 104 to the backboard 102 and/or to immobilize the spine of the individual 104. In one embodiment, the one or more handles 112 or other openings in the backboard 102 are shaped to receive straps or other securing mechanisms.

The backboard 102, in one embodiment, is substantially rigid, and is formed of a durable material. For example, the backboard 102 may comprise a high density polymer, or another durable, rigid material. In certain embodiments, the backboard 102 may be substantially radio-transparent, so that the backboard 102 does not interfere with x-rays or other diagnostic imaging of the individual 104. In a further embodiment, a shell, an upper surface, the one or more handles 112, and/or other portions of the backboard 102 may be formed of a different material than an interior core of the backboard 102, or the like.

The backboard 102, in the depicted embodiment, is a full body backboard that is sized to support a horizontal length of the individual 104. For example, the backboard 102 may be sized to have a length that is as long as or longer than the horizontal length (i.e. the height) of the individual 104. In other embodiments, the backboard 102 may be sized to support the weight of the individual 104, but may be shorter than the horizontal length of the individual. A size of the backboard 102, in one embodiment, is selected based on an intended height, age, size, or other characteristic of individuals 104 for which the backboard 102 is likely to be used, such as infants, children, adults, etc.

In the depicted embodiment, an upper surface of the backboard 102 receives the individual 104 and a scale integrated with the backboard 102 determines a weight of the individual 104. The integrated scale is not shown in the embodiment of FIG. 1, as the scale is embedded within the backboard 102 beneath the upper surface. In other embodiments, the scale may be part of a pad or other layer disposed between the backboard 102 and the individual 104, or the like. In one embodiment, the integrated scale includes one or more load cells that convert the weight of the individual 104 into one or more electrical signals.

In other embodiments, the integrated scale may include one or more spring scales, one or more strain gauge scales, one or more hydraulic scales, one or more pneumatic scales, or another type of scale mechanism capable of integration with a backboard 102. In a further embodiment, the backboard 102 may include one or more additional diagnostic sensors, such as a blood pressure sensor, a temperature sensor, a respiration sensor, a heart rate sensor, a pulse oximeter or other blood-oxygen/SpO$_2$ sensor, and/or another diagnostic sensor to assist a medical technician 106 in caring for an individual 104. An additional diagnostic sensor, in one embodiment, may be integrated with the backboard 102 with the integrated scale. In another embodiment, the backboard 102 may include one or more input/output (I/O) ports and an additional diagnostic sensor may be removably coupled to an I/O port to communicate sensor data to a controller for the backboard 102. The one or more I/O ports may be integrated with the backboard, disposed on the backboard, or the like. An I/O port, in various embodiments, may include a universal serial bus (USB) connection, an IEEE 1394 FireWire connection, an IEEE 802.3 Ethernet connection, an RS-232 serial connection, or the like. In other embodiments, an additional diagnostic sensor may communicate with a controller of the backboard 102 wirelessly using radio frequency (RF) communications, infrared (IR) communications, or the like, such as Bluetooth™ communications, IEEE 802.11 wireless communications (such as Wi-Fi™), IrDA™ specified infrared communications, near field communications (NFC), or the like. The one or more I/O ports (whether wired or wireless), in certain embodiments, are configured to receive sensor data for the individual 104 from the one or more additional diagnostic sensors.

One or more medical technicians 106, such as doctors, nurses, emergency medical technicians (EMTs), firefighters, hospital personnel, hazmat response personnel, or the like, in certain embodiments, may use a determined weight for the individual 104 to administer a therapeutic dosage (i.e. a safe and effective dosage) of a medical treatment to the individual 104. The electronic display device 114, in the depicted embodiment, is disposed on the backboard 102, digitally displaying the determined weight of the individual 104 to a medical technician 106. The electronic display device 114, in various embodiments, may include a liquid crystal display (LCD), a light emitting diode (LED) display, an electronic ink display, and/or another type of electronic display.

One or more user interface devices 116, in the depicted embodiment, are also disposed on the backboard 102 to receive input from a user of the backboard 102, such as the depicted medical technician 106, or the like. The one or more user interface devices 116 may include one or more buttons, one or more switches, one or more dials, a touchscreen, and/or other user interface devices. In one embodiment, user input to the user interface devices 116 initiates a predefined action, such as powering the scale and/or the electronic display device 114 on or off, setting or toggling between measurement units for the displayed weight (e.g. kilograms, pounds, etc.), configuring communications settings for the scale, locking a determined weight on the electronic display device 114, clearing a determined weight from the electronic display device 114, or the like.

In certain embodiments, the one or more user interface devices 116 may be positioned to prevent accidental manipulation of the user interface devices 116 by a medical technician 106 and/or by the individual 104. For example, the one or more user interface devices 116 may include one or more buttons that are embedded slightly below the upper surface of the backboard 102, to prevent accidental button presses, or the like.

In one embodiment, the backboard 102 includes a communications module that communicates a determined weight of the individual 104 to an electronic device 108, 110. In another embodiment, the communications module may receive data from one or more additional diagnostic sensors and/or communicate data from one or more additional diagnostic sensors to an electronic device 108, 110. The depicted electronic devices 108, 110 are remote and separate from the backboard 102 and include a mobile device 108 and a defibrillator 110. Examples of mobile devices 108 include mobile telephone devices, personal digital assistants (PDAs), portable entertainment or gaming devices, and the like. Other embodiments of electronic devices 108, 110 with which the communications module may communicate include computer devices, medical devices, medical treatment systems, and the like.

The communications module, in certain embodiments, communicates with an electronic device 108, 110 wirelessly, using radio frequency (RF) communications, infrared (IR) communications, or the like. For example, the communications module may use Bluetooth™ communications, IEEE 802.11 wireless communications (such as Wi-Fi™), IrDA™ specified infrared communications, near field communications (NFC), or the like. In other embodiments, the communications module may communicate with an electronic device 108, 110 over a wired connection, such as a universal serial bus (USB) connection, an IEEE 1394 FireWire connection, an IEEE 802.3 Ethernet connection, an RS-232 serial connection, or the like. One embodiment of the communications module is described in greater detail below with regard to FIG. 3.

Each electronic device 108, 110, in certain embodiments, includes a communications module, such as a Bluetooth™ module or the like, to receive communications from the communications module of the backboard 102. In one embodiment, an electronic device 108, 110, upon receiving a determined weight of the individual 104, displays the determined weight to a medical technician 106 or other user. In a further embodiment, an electronic device 108, 110 determines a dosage for a treatment for the individual 104 based on a determined weight of the individual 104 in response to receiving the determined weight for the individual 104.

For example, in certain embodiments, the mobile device 108 (or another electronic device) may display a list of determined dosages for various medications based on a received weight for the individual 104, the medical technician 106 may select a medication and the mobile device 108 may display a dosage for the selected medication, or the like. Medications for which dosages are determined by weight include atropine, dopamine, epinephrine, and other medications. In one embodiment, an electronic device 108, 110 determines a dosage based on a stored dosage formula with an input variable for the weight of the individual 104. Dosage formulas may be based on standing orders, on a doctor's recommendation, on a manufacturer's recommendations, or the like. The mobile device 108 or another electronic device may use a software application, firmware, dedicated hardware, or a combination of software, firmware, and/or dedicated hardware to determine and display determined dosages.

The defibrillator 110, in certain embodiments, may receive a determined weight of the individual 104 from the communications module of the backboard 102 and determine a setting for an amount of electrical energy to deliver to the individual 104. The defibrillator 110, in one embodiment, determines an amount of electrical energy (in joules, or the like) to deliver to the individual 104 based on the determined weight of the individual 104 from the backboard 102.

In another embodiment, the defibrillator 110 determines a target, cap, and/or maximum amount of electrical energy to deliver to the individual 104 based on the determined weight. The defibrillator 110 may adjust the target, cap, and/or maximum amount of electrical energy to deliver to the individual 104 based on one or more additional factors. For example, the defibrillator 110 may measure or otherwise determine a resistance, such as a transthoracic impedance, or the like, for the individual 104 and adjust an amount of electrical energy to apply to the individual 104 based on the determined resistance. In a further embodiment, the defibrillator 110 may determine an amount of electrical energy to deliver to the individual 104 based on a determined resistance so that the applied amount of electrical energy does not exceed the determined cap or maximum amount of electrical energy.

In the depicted embodiment, the one or more handles 112 are disposed along a perimeter of the backboard 102, as openings in the backboard 102. In other embodiments, the one or more handles 112 may include one or more attachments coupled to the backboard 102, or the like. The one or more handles 112 facilitate the lifting and/or transporting of the individual 104 using the backboard 102. In certain embodiments, the handles 112 or other openings in the backboard 102 may receive straps or other securing mechanisms to secure the individual 104 to the backboard 102 and/or to immobilize the spine of the individual 104.

Figure 2A:
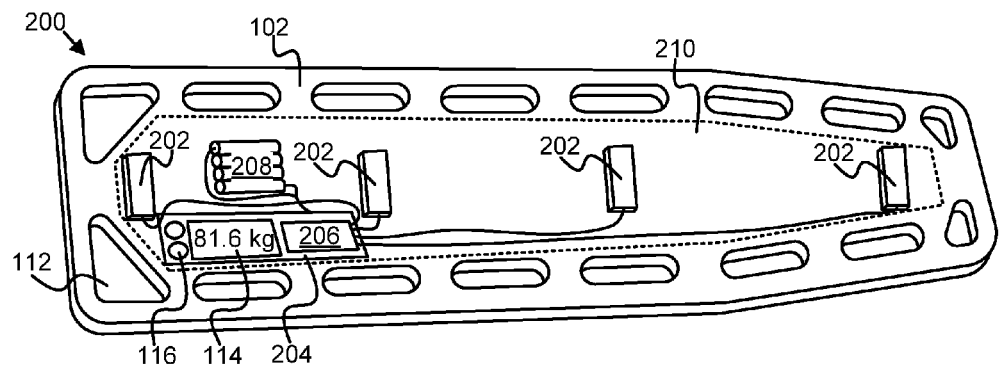
FIG. 2A is a schematic block diagram illustrating one embodiment of a backboard with an integrated scale in accordance with the present invention.
Figure 2B:
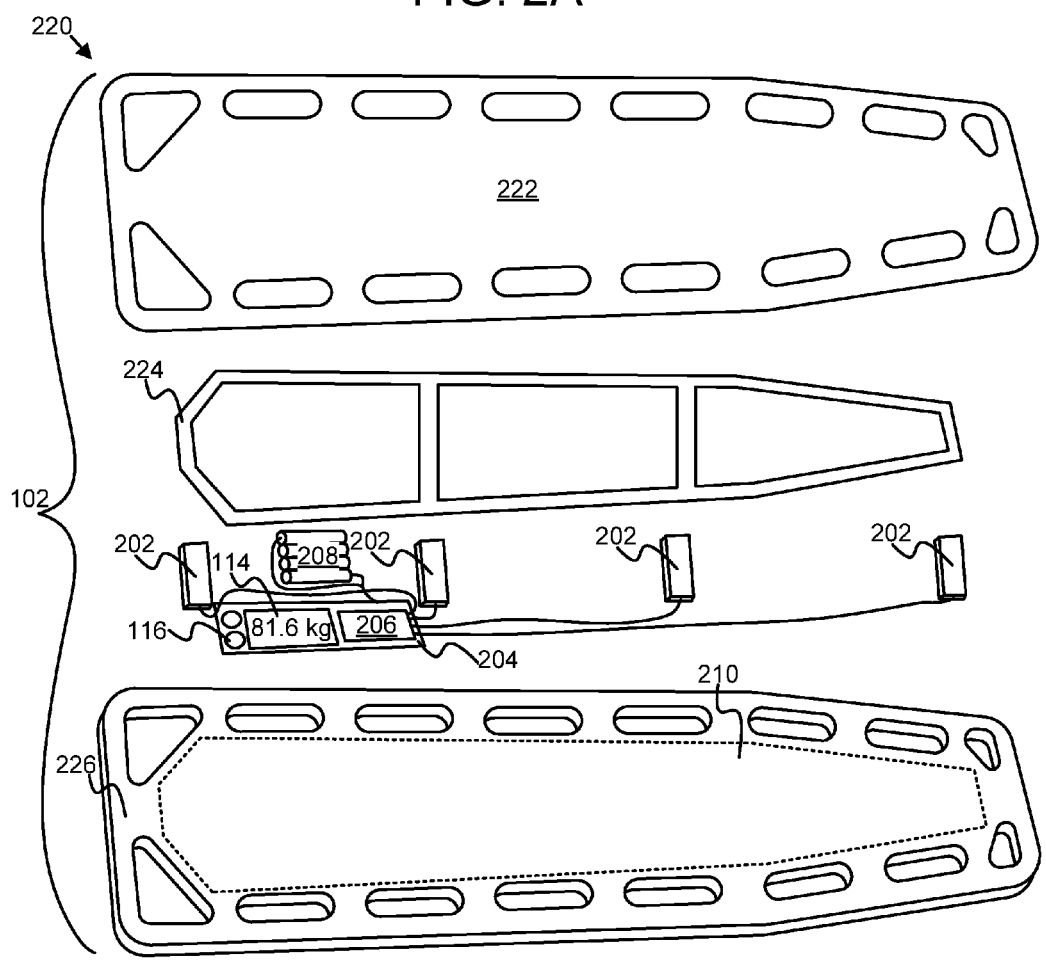
FIG. 2B is an exploded schematic block diagram illustrating another embodiment of a backboard with an integrated scale in accordance with the present invention.

FIG. 2A depicts one embodiment 200 of a backboard 102 with an integrated scale 202. The backboard 102 of FIG. 2A is substantially similar to the backboard 102 of FIG. 1, but with a portion of the upper surface of the backboard 102 removed so that the embedded contents of the backboard 102 are visible. The backboard 102, in the depicted embodiment, includes a scale 202, one or more circuit boards 204, a controller 206, and a power source 208, each of which are disposed with an embedded opening 210 of the backboard 102. One embodiment of an upper surface 222 of the backboard 102 is depicted in FIG. 2B.

In general, the scale 202 determines a weight of an individual 104 in response to an upper surface 222 of the backboard 102 receiving the individual 104. In one embodiment, the scale 202 is embedded within the backboard 102 beneath the upper surface 222 of the backboard 102. In other embodiments, the scale may be part of a pad or other layer disposed between the backboard 102 and the individual 104, or the like.

In the depicted embodiment 200, the scale 202 includes a plurality of load cells that convert a weight of an individual 104 into one or more electrical signals. Examples of load cells include strain gauge load cells, hydraulic load cells, piezoelectric load cells, and the like. While the load cells of the scale 202, in the depicted embodiment 200, are rectangular, in other embodiments, the load cells of the scale 202 may have a circular shape, or another shape to facilitate weighing an individual 104. In other embodiments, the scale 202 may include one or more spring scales, one or more strain gauge scales, one or more hydraulic scales, one or more pneumatic scales, or another type of scale capable of integration with a backboard 102.

Load cell scale mechanisms, in certain embodiments, may be particularly suitable for embedding within a backboard 102 as an embedded scale 202, due to the relatively few moving parts and thin height profile of load cells relative to other types of scale mechanisms. In the depicted embodiment 200, the scale 202 includes four load cell scale mechanisms. In other embodiments, the scale 202 may include a single scale mechanism, two scale mechanisms, three scale mechanisms, or another number of scale mechanisms selected to determine a weight for an individual 104. The number of scale mechanisms, in certain embodiments, may be selected based on a weight rating for the scale mechanisms, an arrangement of the scale mechanisms, within the backboard 102, an architecture of the scale mechanisms, or the like.

A construction type for load cells of the scale 202, in various embodiments, may include a bending beam type, a parallel beam type, a binocular beam type, a canister type, a shear beam type, a single column type, a multi-column type, a pancake type, a load button type, a single ended shear beam type, a double ended shear beam type, an S type, an inline rod end type, a digital electromotive force type, a diaphragm or membrane type, a torsion ring type, a bending ring type, a proving ring type, a load pin type, and/or another construction type suited for determining a weight of an individual 104.

Load cells of the scale 202, in the depicted embodiment 200, are disposed in a linear configuration along a length of the backboard 102. In other embodiments, the load cells of the scale 202 may be disposed toward corners of the backboard 102, toward a perimeter of the backboard 102, or in another configuration to support and determine the weight of an individual 104. A weight support structure 224 that distributes the weight of an individual 104 onto the scale 202 is described below with regard to FIG. 2B.

In one embodiment, one or more circuit boards 204 provide electrical connections and/or mechanical support for the electronic display device 114, the one or more user interface devices 116, the controller 206, and/or the power source 208. The one or more circuit boards 204, in certain embodiments, include several layers, such as insulating layers, conductive layers, structural layers, and the like, and may contain additional electrical components and circuitry.

In various embodiments, the controller 206 receives weight information from the scale 102, controls the visual display of information on the electronic display device 114, receives user input from the one or more user input devices 116, controls communications with one or more electronic devices 108, 110, or the like. The controller 206 may include a processor, a field programmable gate array (FPGA) or other programmable logic device, an application specific integrated circuit (ASIC), and/or other logic hardware. The controller 206, in certain embodiments, may include a computer readable storage medium with executable code to control the visual display of information on the electronic display device 114, receive user input from the one or more user input devices 116, control communications with one or more electronic devices 108, 110, or the like. One embodiment of the controller 206 is described in greater detail below with regard to FIG. 3.

In one embodiment, where the scale 202 includes multiple load cells or other scale mechanisms, the controller 206 combines inputs from the multiple load cells or other scale mechanisms to determine a total weight for an individual 104. For example, the controller 206 may receive multiple inputs from load cells of the scale 202 and sum the inputs in parallel to form a single output weight for an individual 104 that is equal to the sum of the determined forces on the load cells of the scale 202. In embodiments where the backboard 102 includes one or more additional diagnostic sensors, the controller 206 may receive sensor data from the one or more additional diagnostic sensors and display additional diagnostic data on the electronic display device 114, communicate additional diagnostic data to an electronic device 108, 110, or the like.

In one embodiment, the power source 208 provides electric power to the controller 206, the electronic display device 114, the one or more user interface devices 116, the scale 202, and/or other electronic components of the backboard 102. The power source 208 may include one or more batteries, one or more capacitors, a power supply unit (PSU) that converts electric power from another source to a usable form, or the like. In a further embodiment, the backboard 102 includes a charging interface, such as electrical contacts or the like, to charge and recharge the power source 208.

In certain embodiments, the scale 202 and/or the upper surface 222 may be modular and may be removably coupled to and/or removably inserted in an opening 210 of the backboard 102 that is configured to removably receive the scale 202 and/or the upper surface 222. For example, in one embodiment, the scale 202 and the upper surface 222 may be removed from the backboard 102 so that the scale 202 and the upper surface 222 may be used as a modular scale device to determine a weight of a supine individual 104 independently of the backboard 102.

In such modular embodiments, the scale 202 and/or the upper surface 222 may be sized for use with one or more device in addition to the backboard 102, such as an operation table, a medical bed, or the like. In other embodiments, the scale 202 and/or the upper surface 222 may be configured for use directly on a flat surface such as a floor, the ground, a sidewalk, a street, a table, or the like separately from the backboard 102. The backboard 102 may include one or more fasteners, such as latches, locks, snaps, straps, hooks, grooves, or the like, to removably receive and couple the scale 202 and/or the upper surface 222 to the backboard 102. Configuring the scale 202 for modular independent use, in certain embodiments, gives the scale 202 greater adaptability to be used in a wider variety of medical or emergency situations than with the backboard 102 alone, and may also give the scale 202 greater portability, easier storability, or the like.

To facilitate modular or independent use of the scale 202, in one embodiment, at least a portion of the upper surface 222 and of the scale 202 may be flexible, allowing the upper surface 222 and the scale 202 to be compacted by rolling, folding, or the like. For example, in one embodiment, the upper surface 222 may include one or more creases or hinges between elements of the scale 202 allowing the scale 202 and the upper surface 222 to fold and compact along the creases or hinges. In another embodiment, the scale 202 (and optionally one or more associated components such as the electronic display device 114, the controller 206, and the like) may be flexible, comprising one or more flexible thin films or other flexible substrates allowing the scale 202 and the upper surface 222 to be used as a flexible, rollable, mat. In embodiments where at least a portion of the scale 202 and/or the upper surface 222 is flexible, providing for compaction, the scale 202 may be more easily stored and/or transported than when coupled to or non-removably integrated with the backboard 102.

FIG. 2B depicts one embodiment 220 of an exploded view of a backboard 102 with an integrated scale 202. The embodiment 220 of the backboard 102 of FIG. 2B, in certain embodiments, may be substantially similar to the backboard 102 of FIG. 2A and/or the backboard 102 of FIG. 1, but includes an exploded view of an upper surface 222, a weight support structure 224, and a backboard body 226.

In one embodiment, the upper surface 222 receives an individual 104 for weighing and/or providing backboard support. The upper surface 222, in certain embodiments, is at least partially flexible so that the weight of the individual 104 at least partially deforms the upper surface 222 to allow the scale 202 to determine the weight of the individual 104. In various embodiments, the entire upper surface 222 may comprise a flexible material, an interior portion of the upper surface 222 may comprise a flexible material, a perimeter of the upper surface 222 (just within the one or more handles 112, or the like) may comprise a flexible material, or the like, so that the upper surface 222 supports little or no weight of the individual 104.

Due to the varying emergency and medical situations in which the backboard 102 may be used, the upper surface 222, in certain embodiments, is waterproof to protect the scale 202 and/or other electronic components from being damaged by contact with liquid. In a further embodiment, the upper surface 222 is electrically insulating, to protect the scale 202 and/or other electronic components from electric current. For example, in an emergency situation where a medical technician 106 is treating an individual 104 with a defibrillator 110, the upper surface 222 may insulate internal components within the backboard 102 from stray electrical current. In one embodiment, the upper surface 222 includes a polymer material, a rubber material, a treated fabric material, or the like that is flexible, waterproof, and/or electrically insulating.

In one embodiment, the weight support structure 224 interfaces with the upper surface 222 and with the scale 202 to distribute the weight of an individual 104 onto the scale 202. In the depicted embodiment 220, the weight support structure 224 includes a frame that supports at least a portion of the upper surface 222 that supports the weight of an individual 104. As depicted, the frame type weight support structure 224 includes cross braces that distribute the weight of an individual onto the separate scale mechanisms of the scale 202.

In another embodiment, the weight support structure 224 may include several raised ribs. Each raised rib of the weight support structure 225 may be in physical communication with a portion of the scale 202, such as a load cell or other scale mechanism. In embodiments where a raised rib type weight support structure 224 is used, the raised ribs collectively support the weight of an individual 104 and interface with the scale 202 to distribute the weight to the scale 202. In certain embodiments, the weight support structure 224 may be integrated with the upper surface 222.

In the depicted embodiment 220, the backboard body 226 includes an embedded opening 210 to house the scale 202, the one or more circuit boards 204, the controller 206, the power source 208, and/or associated components. The backboard body 226, in one embodiment, is substantially rigid and has a tensile strength sufficient to support an individual 104 during transportation, to immobilize the spine of an individual 104, and the like.

Figure 3:
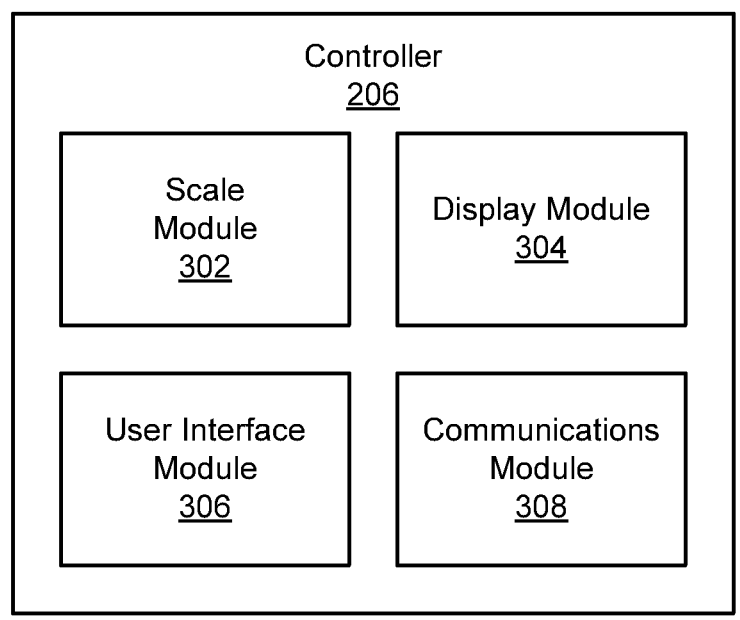
FIG. 3 is a schematic block diagram illustrating one embodiment of a controller in accordance with the present invention.

FIG. 3 depicts one embodiment of a controller 206. In certain embodiments, the controller 206 is substantially similar to the controller 206 of FIG. 2A and FIG. 2B. In the depicted embodiment, the controller 206 includes a scale module 302, a display module 304, a user interface module 306, and a communications module 308.

In one embodiment, the scale module 302 determines a weight for an individual 104 based on input from the scale 202. The scale module 302, in certain embodiments, may receive the weight of an individual 104 from the scale 202. In a further embodiment, the scale module 302 may process or convert weight information from the scale 202 to determine the weight of an individual 104. For example, in one embodiment, the scale module 302 may convert one or more analog sensor signals from the scale 202 to a digital representation of a weight for an individual 104.

In a further embodiment, the scale module 302 may sum or otherwise combine inputs from multiple load cells or other scale mechanisms of the scale 202 to determine a total weight for an individual 104. The scale module 302, in one example embodiment, may receive multiple inputs from load cells of the scale 202 and sum the inputs in parallel to form a single output weight for an individual 104 that is equal to the sum of the determined forces on the load cells of the scale 202, or the like.

In another embodiment, the scale module 302 may calibrate the scale 202 so that the scale module 302 may determine an accurate weight for an individual 104. In one embodiment, the scale module 302 subtracts from the weight of an individual 104 a measured or estimated force that straps or other securing mechanisms place on the individual 104.

In a further embodiment, the backboard 102 may be configured to receive additional medical equipment, such as an automated cardiopulmonary resuscitation (CPR) device or the like, and the scale module 302 subtracts the weight of the additional medical equipment from a total weight measured by the scale 202 to determine a weight of an individual 104. In certain embodiments, the scale module 302 may receive and/or process data from one or more additional diagnostic sensors that are integrated with the backboard 102, such as a blood pressure sensor, a temperature sensor, a respiration sensor, a heart rate sensor, a pulse oximeter or other blood-oxygen/$SpO_2$ sensor, and/or another diagnostic sensor. As described above, in certain embodiments, the backboard 102 may include one or more I/O ports for interfacing with one or more additional diagnostic sensors, and/or may be configured to communicate with one or more additional diagnostic sensors wirelessly.

In one embodiment, the display module 304 controls the visual display of determined weights and/or other information on the electronic display device 114. The display module 304, in certain embodiments, receives a determined weight for an individual 104 from the scale module 302 and displays the determined weight live in real time. In another embodiment, the display module 304 locks or freezes a determined weight for an individual 104 on the electronic display device 114 in response to a predefined user input to the one or more user input devices 116.

In a further embodiment, the display module 304 displays one or more settings for the scale 102, communications information or settings for the communications module 308, information from one or more additional diagnostic sensors integrated with the backboard 102, and/or other relevant information on the electronic display device 114. In certain embodiments, a medical technician 106 or another user may select information for display or otherwise interact with the display module 304 using the one or more user input devices 116.

In one embodiment, the user interface module 306 receives user input from the one or more user interface devices 116. The user interface module 306, in a further embodiment, initiates one or more actions in response to receiving a predefined user input, such as a predefined button press, a predefined menu selection, or the like. For example, the user interface module, in various embodiments, may power the scale 202 and/or associated electronic components on and off, may set measurement units for the scale 202, may configure one or more communications settings for the communications module 308, may instruct the display module 304 to lock and/or record a determined weight or other medical information such as pulse rate, blood pressure, temperature, or the like on the electronic display device 114 or to clear a determined weight or other medical information from the electronic display device 114, or the like.

In one embodiment, the communications module 308 establishes a communications channel between the communications module 308 and an electronic device 108, 110 and communicates a determined weight for an individual 104 to the electronic device 108, 110. In other embodiments, the communications module may communicate additional diagnostic data from one or more additional diagnostic sensors, such as pulse rate data, blood pressure data, temperature data, respiration data, heart rate data, blood-oxygen/$SpO_2$ data, or the like to an electronic device 102, 110. The communications channel may be wireless, such as Bluetooth™ communications, IEEE 802.11 wireless communications (such as Wi-Fi™), IrDA™ specified infrared communications, NFC, or the like, or wired, such as a USB connection, an IEEE 1394 FireWire connection, an IEEE 802.3 Ethernet connection, an RS-232 serial connection, or the like.

In one embodiment, the communications module 308 receives one or more communications settings from a user via the user interface module 306. For example, a user may select an electronic device 108, 110 with which the communications module 308 is to communicate, or the like. In another embodiment, the communications module 308 acts as a server, and receives requests for a determined weight of an individual 104 directly from a client electronic device 108, 110. For example, in various embodiments, the communications module 308 and an electronic device 108, 110 may have a client-server relationship, a peer relationship, a master-slave relationship, or the like.

In certain embodiments, a user, such as a medical technician 106 or the like, may initiate a connection with the communications module 308 from an electronic device 108, 110. In a further embodiment, the communications module 308 may receive user input from an electronic device 108, 110 and may send the user input to the user interface module 306 for processing and/or recording, as described above.

As described above with regard to the electronic devices 108, 110 of FIG. 1, an electronic device 108, 110, upon receiving a determined weight for an individual 104 and/or other diagnostic data, may display the weight and/or other diagnostic data, may determine one or more dosages for treatment of an individual 104, may display a list of determined dosages for various medications, or the like. In a different embodiment, the scale module 302 may determine one or more dosages for treatment of an individual 104 based on a determined weight and/or other diagnostic data, such as a setting for an amount of electrical energy to deliver to the individual 104, dosage of a medication, or the like, and the communications module 308 may communicate the determined one or more dosages to an electronic device 108, 110. In other embodiments, the communications module 308 may communicate additional information, such as information from one or more additional diagnostic sensors integrated with the backboard 102 or the like, to an electronic device 108, 110, the scale module 302 may use additional information to determine a dosage, or the like.

Figure 4:
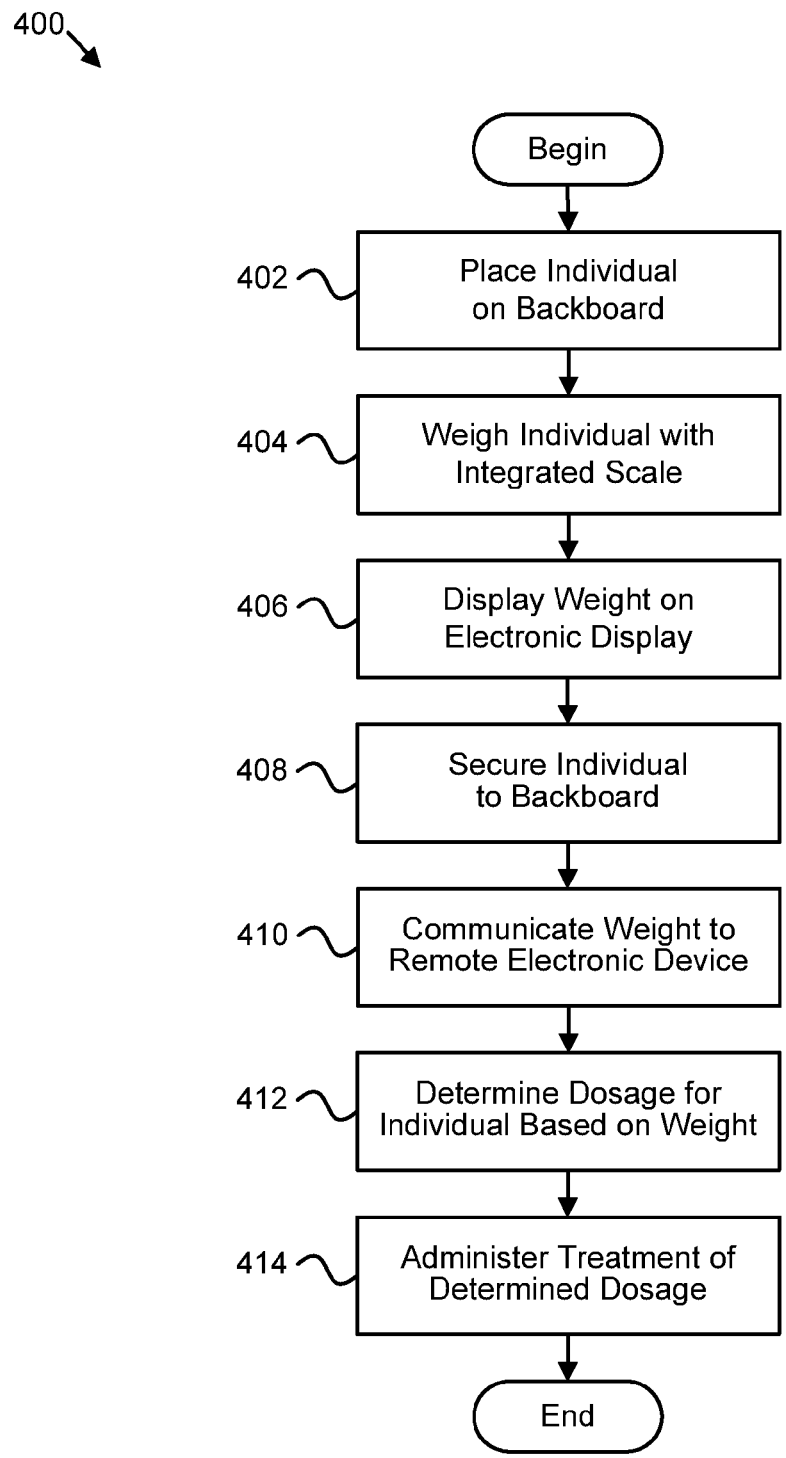
FIG. 4 is a schematic flow chart diagram illustrating one embodiment of a method for weighing an individual on a backboard in accordance with the present invention.

FIG. 4 depicts one embodiment of a method 400 for weighing an individual 104 on a backboard 102. The method 400 begins, and one or more medical technicians 106 place 402 an individual 104 on the backboard 102 in a supine position. The scale module 302 weighs 404 the individual 104 using the scale 202. The display module 304 displays 406 displays the weight of the individual 104 on the electronic display device 114.

One or more medical technicians 106 secure 408 the individual 104 to the backboard 102 to support the individual 104 during transport, to immobilize the spine of the individual 104, or the like. In one embodiment, the securing step 408 is performed after the weighing step 404, such that the scale module 302 may determine a weight for the individual 104 without accounting for the force of straps or other securing mechanisms. In a further embodiment, the securing step 408 is performed prior to the weighing step 404, and the scale module 302 subtracts a measured or estimated force of straps or other securing means to determine 404 a weight for the individual 104.

The communications module 308 communicates 410 the weight of the individual 104 to an electronic device 108, 110, such as a mobile device 108, a defibrillator 110, or the like. The electronic device 108, 110 determines 412 a dosage of a treatment for the individual 104 based on the weight of the individual 104. For example, a mobile device 108 may determine 412 a dosage of one or more medications for the individual, a defibrillator may determine a setting for an amount of electrical energy to deliver to the individual 104, and the like. A medical technician 106 administers 414 a treatment of the determined 412 dosage to the individual 104 and the method 400 ends.

Figure 5:
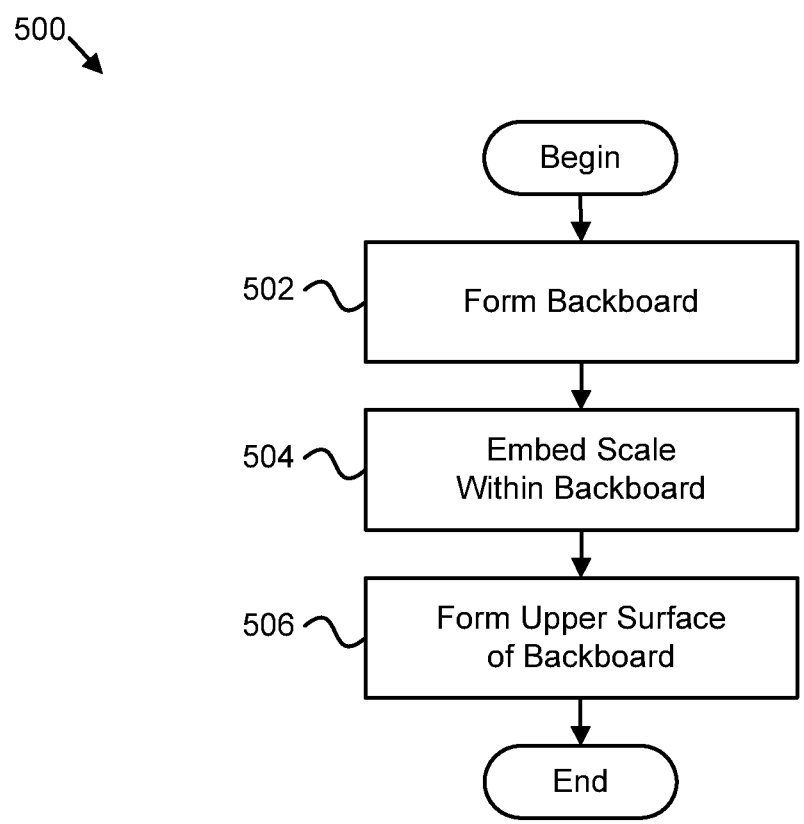
FIG. 5 is a schematic flow chart diagram illustrating one embodiment of a method for forming a backboard with an integrated scale in accordance with the present invention.

FIG. 5 depicts one embodiment of a method 500 for forming a backboard 102 with an integrated scale 202. The method 500 may be performed by a manufacturer which, in various embodiments, may include a technician, an automated device, and/or another entity capable of performing the described steps. The method 500 begins, and a manufacturer forms 502 a backboard 102 configured to support a supine individual 104 during transportation. The manufacturer embeds 504 a scale 202 within the backboard 102. The embedded scale 202 is configured to determine a weight of a supine individual 104 in response to the backboard 102 receiving the supine individual 202. The manufacturer forms 506 an upper surface 222 of the backboard 102. The upper surface 202 is configured to receive a supine individual 104 and the scale 202 is embedded beneath the upper surface 222.

In other embodiments, the method 500 may include the manufacturer performing one or more additional steps not depicted in FIG. 5 for forming and/or installing other elements of the backboard 102 and associated system 100 described herein. For example, in various embodiments, the method 500 may include the manufacturer disposing one or more electronic display devices 114 on the backboard 102, disposing one or more user interface devices 116 on the backboard 102, embedding a controller 206 and/or a communications module 308 within the backboard 102 in communication with the scale 202, configuring an electronic device 108, 110 remote from the backboard 102 for interfacing with the communications module 308, embedding a weight support structure 224 within the backboard 102 interfacing with the upper surface 222 and the scale 202, forming a plurality of handles 112 along a perimeter of the backboard 102, and/or other steps for forming or manufacturing a backboard 102 as described herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to weigh an individual, the apparatus comprising:
   a backboard configured to support an immobilized, supine individual while the backboard is lifted during transportation of the supine individual;
   an integral upper surface of the backboard, the upper surface configured to receive the supine individual; and
   a scale embedded integrally within a rigid body of the backboard beneath the upper surface, the embedded scale configured to determine a weight of the supine individual in response to the upper surface receiving the supine individual with the supine individual lying horizontally flat on the upper surface, the upper surface being at least partially flexible such that the weight of the supine individual at least partially deforms the upper surface to place the weight of the supine individual on the embedded scale within the rigid body of the backboard.

2. The apparatus of claim 1, further comprising an electronic display device disposed on the backboard, the electronic display device configured to display the determined weight of the supine individual.

3. The apparatus of claim 1, further comprising a communications module embedded within the backboard, the communications module configured to communicate the determined weight of the supine individual to an electronic device, the electronic device remote from the backboard.

4. The apparatus of claim 3, wherein the electronic device is configured to determine a dosage for a treatment for the supine individual based on the determined weight of the supine individual.

5. The apparatus of claim 4, wherein the electronic device comprises a defibrillator configured to receive the determined weight of the supine individual and the dosage comprises a setting for an amount of electrical energy that the defibrillator delivers to the supine individual.

6. The apparatus of claim 4, wherein the treatment comprises a medication and the electronic device is configured to display the determined dosage of the medication to a user of the electronic device.

7. The apparatus of claim 1, further comprising one or more input/output ports integrated with the backboard, the one or more input/output ports configured to receive sensor data for the supine individual from one or more additional diagnostic sensors.

8. The apparatus of claim 1, further comprising one or more user interface devices disposed on the backboard, the one or more user interface devices configured to receive input from a user of the backboard, wherein the one or more user interface devices are configured to initiate at least one action selected from the group consisting of powering the scale on and off, setting measurement units for the determined weight, configuring communications settings for the scale, locking the determined weight on an electronic display device, and clearing the determined weight from an electronic display device.

9. The apparatus of claim 1, further comprising a weight support structure interfacing with the upper surface to distribute the weight of the supine individual onto the embedded scale.

10. The apparatus of claim 9, wherein the weight support structure comprises a plurality of raised ribs, each raised rib in physical communication with a portion of the scale, the plurality of raised ribs collectively configured to support the weight of the supine individual.

11. The apparatus of claim 9, wherein the weight support structure comprises a frame that supports at least a portion of the upper surface supporting the weight of the supine individual, the frame distributing the weight of the supine individual onto the embedded scale.

12. The apparatus of claim 1, wherein the scale comprises one or more load cells configured to convert the weight of the supine individual into one or more electrical signals.

13. The apparatus of claim 1, wherein the backboard comprises a full body backboard sized to support a horizontal length of the supine individual.

14. A system to weigh an individual, the system comprising:
   a backboard configured to support an immobilized, supine individual while the backboard is lifted during transportation of the supine individual;
   an electronic device remote from the backboard;
   an integral upper surface of the backboard, the upper surface configured to receive the supine individual;

a scale embedded integrally within a rigid body of the backboard beneath the upper surface, the embedded scale configured to determine a weight of the supine individual in response to the upper surface receiving the supine individual with the supine individual lying horizontally flat on the upper surface, the upper surface being at least partially flexible such that the weight of the supine individual at least partially deforms the upper surface to place the weight of the supine individual on the embedded scale within the rigid body of the backboard; and a communications module embedded within the backboard, the communications module configured to communicate the determined weight of the supine individual to the electronic device.

15. The system of claim 14, wherein the electronic device is configured to determine a dosage for a treatment for the supine individual based on the determined weight of the supine individual.

16. The system of claim 15, wherein the electronic device comprises a defibrillator configured to receive the determined weight of the supine individual and the dosage comprises a setting for an amount of electrical energy that the defibrillator delivers to the supine individual.

17. The system of claim 15, wherein the treatment comprises a medication and the electronic device is configured to display the determined dosage of the medication to a user of the electronic device.

18. A method for forming a backboard with an integrated scale, the method comprising:

forming a backboard configured to support an immobilized supine individual while the backboard is lifted during transportation of the supine individual;

embedding a scale integrally within a rigid body of the backboard, the embedded scale configured to determine a weight of the supine individual in response to the backboard receiving the supine individual with the supine individual lying horizontally flat on the upper surface; and forming an integral upper surface of the backboard, the upper surface configured to receive the supine individual, the scale embedded beneath the upper surface, the upper surface being at least partially flexible such that the weight of the supine individual at least partially deforms the upper surface to place the weight of the supine individual on the embedded scale within the rigid body of the backboard.

19. The method of claim 18, further comprising embedding a communications module within the backboard, the communications module in communication with the scale.

20. The method of claim 19, further comprising configuring an electronic device for interfacing with the communications module, the electronic device remote from the backboard.

* * * * *